United States Patent [19]

Horecker

[11] 4,388,234

[45] Jun. 14, 1983

[54] PEPTIDE ISOLATION

[75] Inventor: Bernard L. Horecker, New York, N.Y.

[73] Assignee: Hoffmann-La Roche Inc., Nutley, N.J.

[21] Appl. No.: 335,001

[22] Filed: Dec. 28, 1981

[51] Int. Cl.³ .................... C07C 103/52; A61K 37/02
[52] U.S. Cl. .............................. 260/112.5 R; 424/177
[58] Field of Search .................. 424/177; 260/112.5 R

[56] References Cited

U.S. PATENT DOCUMENTS

| | | | |
|---|---|---|---|
| 4,010,148 | 3/1977 | Goldstein | 260/112.5 R |
| 4,079,127 | 3/1978 | Goldstein et al. | 424/177 |
| 4,082,737 | 4/1978 | McGregor et al. | 260/112.5 R |
| 4,128,637 | 12/1978 | Naylor et al. | 424/177 |
| 4,239,498 | 12/1980 | Rule | 424/177 |
| 4,250,084 | 2/1981 | Trainin | 424/177 |

OTHER PUBLICATIONS

Low et al., Proc. Nat. Acad. Sci. 78, 1162-1166 (1981).
Goldstein et al., Proc. Nat. Acad. Sci. 69, 1800-1803 (1972).
Goldstein et al., Proc. Nat. Acad. Sci. 74, 725-729 (1977).
Low et al., J. Biol. Chem. 254, 981-986 (1979).
Hooper et al., Annals New York Academy of Sciences 249, 125-144 (1975).

*Primary Examiner*—Delbert R. Phillips
*Assistant Examiner*—F. T. Moezie
*Attorney, Agent, or Firm*—Jon S. Saxe; George M. Gould; Peter R. Shearer

[57] ABSTRACT

A process for isolating selected polypeptides from biological specimens. The process employs a guanidinium salt to treat frozen biological specimens from which selected polypeptides are to be obtained. The process is useful in reducing proteolytic modification of the selected polypeptides.

24 Claims, No Drawings

PEPTIDE ISOLATION

BACKGROUND OF THE INVENTION

Many major advances in pharmacology have been due to the isolation and identification of proteins or polypeptides endogenous to biological systems.

For example polypeptides isolated from thymus tissue are significant pharmacologically because of their roles in developing, maintaining, restoring or stimulating the immune response and competence in animals, including man.

In particular a fraction has been prepared from calf thymus extracts and designated Thymosin Fraction 5. Studies have shown that Thymosin Fraction 5 is a potent immunopotentiating preparation and that it can act in lieu of the thymus gland to reconstitute immune functions in thymic deprived immunodeficient individuals. Peptides which have been isolated from Thymosin Fraction 5 include thymosin $\alpha_1$, an acidic peptide containing 28 amino acid residues, the structure of which has been described in U.S. Pat. No. 4,079,127, and thymosin $\beta_4$ containing 44 amino acid residues, the structure of which has been described in Low, T.L.K., et al., Proc. Nat. Acad. Sci. 78, 1162–1166 (1981).

Another peptide, designated thymosin $\beta_8$ and having the formula

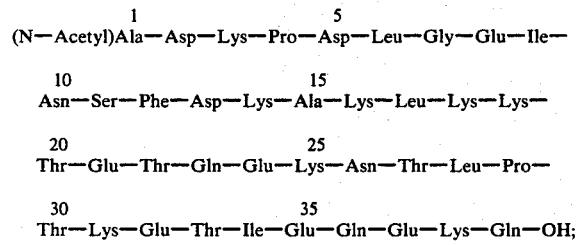

has also been isolated from Thymosin Fraction 5. The structure and isolation of thymosin $\beta_8$ has been disclosed in U.S. patent application Ser. No. 334,420, filed on Dec. 24, 1981, with common inventorship, and entitled Immunopotentiating Peptides from Thymus.

Thymosin Fraction 5 has been isolated from calf thymus by the procedure of Goldstein et al., Proc. Nat. Acad. Sci. 69, 1800–1803 (1972) and thymosin $\alpha_1$, thymosin $\beta_4$ and thymosin $\beta_8$ were prepared from the isolated Thymosin Fraction 5 by methods well known in the art and purified to be essentially free of other proteinacious substances as by conventional chromatographic methods such as by a combination of ion-exchange chromatography and gel filtration as by the methods described by Goldstein et al., Proc. Nat. Acad. Sci. USA 74, 725–729 (1977), Low et al., J. Biol. Chem. 254, 981–986 (1979) and Low et al., Proc. Nat. Acad. Sci. USA 78, 1162–1166 (1981).

DETAILED DESCRIPTION OF THE INVENTION

The present invention relates to a process for reducing proteolytic modification of polypeptides selected for isolation from biological specimens. Particularly the invention relates to a process which employs an anti-proteolytic agent to treat a frozen biological specimen. As a result of this treatment polypeptides can be isolated from the specimen, which polypeptides would otherwise be absent or present in much less significant amounts.

More particularly in the process of the invention, selected polypeptides may be isolated from a freshly frozen biological specimen by treating the specimen with an effective amount of a guanidinium salt (the anti-proteolytic agent) and thereafter separating the selected polypeptides from the specimen.

The present invention also relates to an active peptide fraction (designated APF) containing immunopotentiating thymic polypeptides having molecular weights of about 10,000 daltons or less and isolated from freshly frozen thymic tissue by a process comprising treating the tissue with an effective amount of a guanidinium salt.

The biological specimen may be any biological tissue or cells therefrom or fluids. Among such tissues there are included for example thymus, spleen, heart, brain, liver, lung, kidney and the like, or cells therefrom. Among such fluids there are included for example, blood, urine, lymph, etc. The tissues or fluids may be obtained from any animal such as fish or mammals for example, mouse, rat, calf, sheep, pig, dog, etc. The preferred biological specimen is tissue. The preferred source of tissue for the invention process is the calf thymus.

It is essential for the process of the invention, including obtaining APF, that the biological specimen, where such specimen is tissue for example, be collected at the time of slaughter of the animal, providing fresh tissue which is immediately frozen by any conventional method as under liquid $N_2$ or in dry ice. The tissue may be stored in its frozen state until further use, i.e. treatment with the anti-proteolytic agent embraced by this invention.

In preparing the frozen tissue or other biological specimen in order to obtain selected polypeptides therefrom, it is essential that the tissue or other biological specimen remain frozen when treated with the anti-proteolytic agent. For example the frozen tissue may be pulverized in the presence of an ice cold solution of the antiproteolytic agent or separately pulverized while frozen and the resulting frozen powder added to an ice cold solution of the anti-proteolytic agent with conventional mechanical agitation. Where the biological specimen is in the form of whole cells, no pulverization is necessary before or during treatment with the anti-proteolytic agent.

After treatment of the frozen tissue with the anti-proteolytic agent, the treated tissue can be submitted to any conventional isolation and purification processes for separating polypeptides, as for example preparative isoelectric focusing, chromatography, electrophoresis, ultrafiltration and the like. The preferred isolation procedure is by ultrafiltration and high pressure liquid chromatography (HPLC).

The anti-proteolytic agent of this invention may be any guanidinium salt. Among such guanidinium salts there are included the organic acids such as for example acetic acid and the mineral acids such as for example the hydrohalides, i.e. hydrobromide, hydrochloride, hydrofluoride and hydroiodide, or thiocyanate. The preferred guanidinium salt is guanidine hydrochloride. The concentration of guanidinium salt in the treatment of the tissue is not critical in that any effective amount may be used. It is preferred, however, that a 3 to 6 M solution of the guanidinium salt be used for treating the tissue and that about 3 to 9 volumes of the salt solution per gram of tissue be used. The concentration of the salt may be achieved by making the salt up in a solvent such as water or aqueous buffers, such as ammonium acetate, pyridine acetic acid, and the like.

When the process of the present invention was employed in preparing APF from thymus tissue, it was surprisingly observed on the one hand that thymosin $\alpha_1$ and thymosin $\beta_8$ did not occur in significant concentrations.

On the other hand, it was observed that thymosin $\beta_9$ having the formula

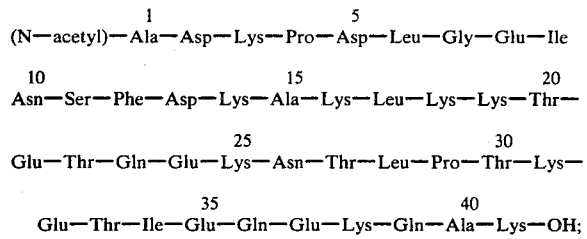

did not occur in significant concentrations in preparations of Thymosin Fraction 5 prepared by extraction in the absence of treatment with the anti-proteolytic agent. It would appear, therefore, that thymosin $\alpha_1$ and thymosin $\beta_8$ are products occurring by proteolytic modification. For example, it appears that thymosin $\beta_8$ is a product occurring by proteolytic modification of thymosin $\beta_9$.

It was further observed that thymosin $\beta_4$ occurred in very appreciable amounts whether the tissue was extracted in the presence or in the absence of the anti-proteolytic agent.

In the isolation of the polypeptides, thymosin $\beta_4$ and thymosin $\beta_9$, it is preferred that these polypeptides be isolated from frozen calf thymus after treatment with the anti-proteolytic agent as described earlier. Subsequent to extraction of the tissue with the solution containing the anti-protoelytic agent it is preferred that thymosin $\beta_4$ and thymosin $\beta_9$ be isolated by ultrafiltration and by column chromatography employing a reverse phase hydrophobic resin. Any reverse phase hydrophobic resin may be employed in a conventional manner. Among such resins there are included for example a hydrocarbon ($C_8$ to $C_{18}$) on any inert matrix such as silica gel, glass, polysaccharides and the like, which matrix is inert to the eluting agent being employed. The preferred resin is a straight chain $C_{18}$ hydrocarbon bonded to silica gel beads or glass beads.

The eluting agent may be any miscible solvent eluting the selected peptides to be isolated. For example the eluting solvent for thymosin $\beta_4$ and thymosin $\beta_9$ may be solvents selected from the lower alkanols such as propanol or from nitriles such as acetonitrile, or organic acids such as trifluoroacetic acid. The preferred eluting solvent is propanol, preferably employed in the presence of a buffer such as aqueous pyridine-formic acid. In such solvent thymosin $\beta_9$ emerges from HPLC immediately after thymosin $\beta_4$ which may be separated from thymosin $\beta_9$ by converting thymosin $\beta_4$ to the sulfoxide using the method of Neumann in *Methods of Enzymatic analysis*, 25,395 (1972).

The purity of the polypeptides obtained by the procedures described herein may be determined conventionally by any recognized conventional analytical method such as by ultracentrifugation, gel electrophoresis or chromatography. The identity of the purified polypeptide may be determined by any conventional amino acid analysis procedure or by sequencing.

Amino acid analyses of the polypeptides disclosed herein may be carried out with an amino acid analyzer modified for derivitization with o-phthalaldehyde in accordance with the method of Benson, et al., Proc. Nat. Sci. 72, 619–622 and with a conventional fluorescence detector. Proline may be determined with an amino acid analyzer employing a fluorescamine detector system after oxidation with N-chlorosuccinamide in accordance with the method of Weigele, et al., Biochem, Biophys. Res. Commun. 50, 352–356 (1973). Carboxypeptidase A treatment may be carried out at room temperature for 2 hours in 0.2 M pyridine (pH 7.4) with a ratio of polypeptide to carboxypeptidase of 12.5:1 (w/w). The released amino acids may be analyzed by HPLC on an Ultrosphere-ODS column after prelabeling with o-phthaladehyde in accordance with the method of Jones, et al., J. Liquid Chromatography 4, 565–586 (1981).

Enzymatic digestion of thymosin $\alpha_1$, thymosin $\beta_4$, thymosin $\beta_8$ and thymosin $\beta_9$ for sequence determinations may be performed in conventional manner as by mild acid hydrolysis in 30 mM HCl at 105° C. for 15 hours as described by Schultz, Methods in Enzymology, Vol. XI, pp. 255–263 (1967), or by using trypsin and/or Staph aureus protease V8 added to the purified polypeptide. Separation and analysis of the acid hydrolysates or enzymatic digests may be performed conventionally by HPLC. The amino acid sequences of the separated peptides may be determined by the manual Edman degradation procedures, Tarr et al., Methods in Enzymology, Vol. XLVII, 335–357 (1977).

In one aspect of the invention the polypeptides, thymosin $\beta_4$ and thymosin $\beta_9$, may be isolated from frozen thymus tissue by a process which encompasses, for example, extraction of the polypeptides by the following steps:

(1) homogenizing the tissue in the presence of an ice cold aqueous solution containing an effective amount of guanidine hydrochloride, (2) suspending the resulting homogenate in a pyridine-formic acid buffer solution at about pH 4.0, (3) centrifuging the resulting suspension and obtaining the resulting supernatant, (4) ultrafiltering the resulting supernatant through ultrafilters having a molecular weight cut-off of 10,000 daltons, (5) submitting the resulting filtrate to a chromatographic column utilizing a reverse phase hydrophobic resin, (6) washing the resin with pyridine-formic acid buffer solution of about pH 4.0, (7) collecting the material eluting from said resin upon applying the same buffer containing 40% by volume n-propanol, and (8) isolating the polypeptides, thymosin $\beta_4$ and thymosin $\beta_9$ from the resulting 40% n-propanol eluate of step (7) by high pressure liquid chromatography (HPLC) utilizing a reverse phase hydrophobic resin and eluting with a gradient of increasing concentrations of n-propanol from 0 to 40% by volume in the aforesaid buffer.

In step (8) above thymosin $\beta_9$ emerges from the HPLC immediately after thymosin $\beta_4$. In order to more completely separate thymosin $\beta_4$ from thymosin $\beta_9$, the eluate from step (8) containing the aforesaid polypeptides is collected and thymosin $\beta_4$ therein is converted to the sulfoxide using the method described earlier. The sulfoxide form of thymosin $\beta_4$ is then separated easily from thymosin $\beta_9$ by HPLC utilizing a reverse phase hydrophobic resin and eluting with a gradient of increasing concentrations of n-propanol from 0 to 40% by volume in the pyridine-formic acid buffer solution of about pH 4.0.

In another aspect of the invention the APF disclosed herein may be obtained from frozen calf thymus by following steps (1) through (7) above. After step (7) the resulting 40% n-propanol eluate therefrom constitutes the APF fraction and material. This APF material may be collected, lyophilized and stored as a dry powder until further use. To futher use the dry powder form of the APF, the powder may be reconstituted in water, preferrably in a saline solution.

The APF disclosed herein as can be demonstrated by the polypeptides contained in the APF, i.e. thymosin $\beta_4$ and thymosin $\beta_9$, has activity in the restoration and stimulation of immune function. Thus, APF is useful, for example, in the treatment of opportunistic infections in an immunosuppressed animal when administered to the animal in an immunopotentiating effective amount.

More particularly the APF and polypeptides contained therein as disclosed herein and the pharmaceutically acceptable acid addition salts or base salts of such polypeptides may be used as medicaments; for example, in the form of pharmaceutical preparations which contain them in association with a compatible pharmaceutical carrier material. This carrier material may be sterile water or saline suitable for parenteral administration (e.g. intravenous, subcutaneous or intramuscular). The pharmaceutical preparations may be subjected to conventional pharmaceutical operations, such as sterilization and may contain conventional adjuvants, such as preservatives, stabilizers, wetting agent and the like.

The pharmaceutical preparations can be prepared according to methods well known in the art. They can be administered parenterally from once a day up to four times a day. The parenteral dosage form preferably contains 10 ng-100 $\mu$g of active ingredient per kg of body weight.

The polypeptides, i.e. thymosin $\beta_4$ and thymosin $\beta_9$, disclosed herein were isolated free of other proteinaceous material and tested for protective activity against opportunistic infections in immunosuppressed mice. Female ddY mice (6 weeks old) weighing about 25 g were pretreated daily for eight days with 5-fluorouracil (5-FU) (25 mg/kg/day, i.p.) with thymosin $\alpha_1$, thymosin $\beta_4$, thymosin $\beta_8$, or thymosin $\beta_9$ in varying dosages. The mice were then infected with Candida albicans ATCC 10231 ($1 \times 10^5$ cells or more) at 24 hours after the last treatment. One control group was administered 5-FU and saline solution and a second control group received neither 5-FU nor a thymic polypeptide prior to infection with Candida albicans. The number of animals surviving eight days after infection with Candida albicans and 15 days after infection with Candida albicans is presented in Table I.

As can be seen from Table I, treatment with 5-FU made the mice susceptible to the infection with Candida albicans, while the control group which did not receive 5-FU pretreatment was highly resistant to infection. The protective effects against infection which were conferred by the polypeptides i.e. thymosin $\beta_4$ and thymosin $\beta_9$ contained in APF, are of comparable similar magnitude to the polypeptides of Thymosin Fraction 5, i.e. thymosin $\alpha_1$ and thymosin $\beta_8$.

TABLE I

| | Dose $\mu$g/kg/day | Survivors at Day 8 | Day 15 | P* |
|---|---|---|---|---|
| Thymosin $\beta_1$ | 4 | 7/10 | 6/10 | 0.0001 |
| | 40 | 7/10 | 7/10 | <0.0001 |
| Thymosin $\beta_4$ | 0.4 | 7/10 | 6/10 | <0.0001 |
| | 4 | 5/10 | 5/10 | 0.0007 |
| | 40 | 1/10 | 1/10 | |
| Thymosin $\beta_8$ | 0.4 | 9/9 | 9/9 | <0.0001 |
| | 4 | 8/9 | 8/9 | <0.0001 |
| | 40 | 7/9 | 7/9 | <0.0001 |
| Thymosin $\beta_9$ | 0.04 | 4/10 | 4/10 | <0.003 |
| | 0.4 | 7/10 | 6/10 | <0.0001 |
| | 4 | 3/10 | 3/10 | <0.003 |
| | 40 | 4/10 | 4/10 | <0.004 |
| Control (5-FU) | | 10/10 | 10/10 | |
| Control | | 1/10 | 1/10 | |

*Rank sum test

The following examples further elucidate the invention but are not meant to restrict the invention in scope or spirit.

EXAMPLE 1

Preparation of thymosin $\beta_4$ and thymosin $\beta_8$

A sample of thymosin Fraction 5 (1.2 g) was dissolved in 100 ml of 2% ampholine for separation in the pH range 4-6 and filtered through a 0.45 $\mu$m Millipore HA filter. After addition of 4 g of Ultrodex the gel was cast onto a glass plate (11 $\times$ 24.5 cm) and electrofocused for 16 h over the long direction at 8° C. and 8 W, maintaining the voltage below 1.5 kV and the current below 20 mA. The focused gel was cut with a grid into 30 sections, each of which was eluted on a small column with 5 ml of $H_2O$. The pH of eluate was determined at 0° C. For analysis by HPLC 5 $\mu$l aliquots of each eluate were applied to a RP18 column (Ultrasphere-ODS, 5$\mu$, 4.6$\times$250 mm) equilibrated with 0.2 M pyridine-1 M formic acid, containing 0.05% thiodiglycol (v/v) at a flow rate of 0.7 ml/min. The peptides were eluted with the same buffer containing n-propanol, the concentration of which was increased by 4% every 10 minutes to a final concentration of 40% (v/v). At 10 second intervals 5 $\mu$l samples were diverted to the fluorescamine detector. For the preparative runs, twelve 450 $\mu$l aliquots of the eluates from slices 12-15 were injected successively on to the same RP-18 column used for the analytical runs and the peptides eluted with the same buffer and n-propanol gradient. Fractions (0.7 ml) were collected every 2 minutes and aliquots (5 $\mu$l of a 1:25 dilution) of each aliquot analyzed by direct injection into the borate buffer line of the fluorescamine detector, because the automatic column monitoring was off-scale. Fractions found to contain the peptides corresponding to thymosin $\beta_4$ and thymosin $\beta_8$ were separately pooled and lyophilized.

EXAMPLE 2

Trypsin Digestion of Thymosin $\beta_4$ and Thymosin $\beta_8$

Digestion with trypsin was carried out in 200 $\mu$l volumes containing 400 $\mu$g of thymosin $\beta_4$ or 312 mg of thymosin $\beta_8$ and 20 $\mu$g of trypsin in 0.4 M pyridine, pH 7.5. After 14 h at room temperature the reactions were terminated by the addition of 15.2 $\mu$l of concentrated HCOOH and injected on to the Ultrasphere-ODS column, followed by 0.2 M pyridine-1 M formic acid at a flow rate of 0.37 ml/min. Elution was with a gradient of CH$_3$CN, increasing from 0 to 40% (v/V) over a period of 2h. Aliquots (5 μl) were diverted to the fluorescamine detection system every 20 seconds. Fractions were collected every 2 minutes. The major peaks were collected and analyzed. The minor peaks were identified as products of incomplete digestion.

Digestion of thymosin $\beta_4$ or thymosin $\beta_8$ with *Staph aureus* Protease V8 was carried out in 40 μl reaction mixtures containing 0.1 M NH$_4$HCO$_3$, pH 7.8, 2 mM EDTA and a ratio of peptide to protease of 30:1 (w/w). After incubation for 14 h at 25° C. the solutions were diluted to 400 μl with 0.2 M pyridine-1 M formic acid and the peptides separated conventionally on an RP18 column. In this experiment 6.98 μmol of peptide was digested.

The peptides derived from digestion with trypsin and with *Staph aureus protease* V8 were isolated and analyzed by HPLC.

EXAMPLE 3

Preparation of APF, thymosin $\beta_4$ and thymosin $\beta_9$

Calf thymus collected at the time of slaughter was cut into 60 g pieces and immediately frozen and stored in dry ice. The frozen tissue was pulverized and the frozen powder added with mechanical stirring to nine volumes of ice-cold 6M guanidine hydrochloride solution. The suspension was then blended at high speed in a large Waring blender or similar device. This suspension was then treated with pyridine to a final concentration of 0.2M and with formic acid to a final concentration of 1M. The suspended material was removed by centrifugation and the supernatant solution filtered successively through Whatman No. 541 and Whatman No. 1 filters. The clear solution was pumped through a hollow fiber concentration system (Amicon DC2, H1P10 cartridge). The ultrafiltrate emerging from the hollow fiber system was pumped onto a prepackaged reverse phase RP18 column, at a rate of flow balanced against that of effluent from the hollow fiber system. The effluent from the column was returned for recycling to the reservoir feeding the DC2 hollow fiber system. Adsorption of peptides can be determined by analysis by HPLC of aliquots of the solution emerging in the H1P10 ultrafiltrate. When adsorption was complete, the RP18 column was washed with 0.4M pyridine-0.5M formic acid (pH 4.0) to remove salts and the peptides were eluted with 40% n-propanol in 0.4M pyridine-0.5M formic acid, pH 4.0. The quantity of eluting solution contains the APF material and was approximately 350 ml for each 100 g of thymus tissue extracted. The solution containing the APF material which contains thymosin $\beta_4$ and thymosin $\beta_9$, was lyophylized and stored as a dry powder.

To isolate and separate thymosin $\beta_4$ and thymosin $\beta_9$, advantage was taken of the presence of methionine in the former. The lyophylized APF material was dissolved in 5 ml of 0.2M pyridine-1 M HCOOH and oxidized for 45 minutes at room temperature with one-half volume of 30% H$_2$O$_2$. The sulfoxide form of thymosin $\beta_4$ was then recovered by reverse phase HPLC which also yielded the peptide, thymosin $\beta_9$ which emerges immediately after the sulfoxide form of thymosin $\beta_4$ on HPLC. Thymosin $\beta_9$ was found to be similar to thymosin $\beta_4$ in amino acid composition, but it did not contain methionine.

Reduction of oxidized thymosin $\beta_4$ was carried out with 20% mercaptoethanol under argon for 24 h at 37° C. The recovery of the reduced peptide, now free of containing peptides, was 70%. The structure of thymosin $\beta_4$ and thymosin $\beta_9$ recovered the foregoing procedure was confirmed by its amino acid composition and by the separation and analysis of tryptic peptides.

Based on the results of the direct analysis of aliquots from several different preparations the quantity of thymosin $\beta_9$ yield was 8–18 μg/g tissue. The quantity of thymosin $\beta_4$ present in calf thymus was in the range of 35–80 μg/g tissue. This is to be compared with a value of 4.1 μg of thymosin $\beta_4$ per gram of thymus gland calculated from the quantities recovered from thymosin Fraction 5 as reported by Low et al in Proc. Nat. Acad. Sci. 78, 1162–1166 (1981).

EXAMPLE 4

Tryptic Digestion of Thymosin $\beta_9$

Thymosin $\beta_9$ was digested by trypsin and *S. aureus* protease following the procedure of Example 2.

I claim:

1. An active peptide fraction containing immunopentatiating thymic polypeptides, prepared from freshly frozen thymic tissue by a process comprising:
   (a) homogenenizing the frozen tissue in an aqueous cold solution containing an effective amount of a guanidinium salt, and
   (b) isolating from the resulting homogenate the peptide material therein by an isolation method comprising ultrafiltration through ultrafilters having a molecular weight cut-off of 10,000 daltons and adsorption on and elution from a reverse phase hydrophobic resin with a miscible solvent capable of eluting and providing thereby the active peptide fraction.

2. A fraction according to claim 1 wherein the polypeptides contained by said fraction comprise thymosin $\beta_4$ and thymosin $\beta_9$.

3. A fraction according to claim 1 wherein the thymic tissue is calf thymus or calf spleen.

4. A fraction according to claim 1 wherein the guanidinium salt is a guanidine hydrohalide.

5. A fraction according to claim 4 wherein the guanidine hydrohalide is guanidine hydrochloride.

6. A fraction according to claim 1 wherein said resin is a hydrocarbon of C$_8$ to C$_{18}$ on an inert matrix, said matrix being inert to said solvent.

7. A fraction according to claim 6 wherein the inert matrix is selected from the group consisting of silica gel, glass and polysaccharides.

8. A fraction according to claim 1 wherein said fraction is obtained from said resin by eluting said resin with a pyridine-formic acid buffer solution of about pH 4.0, said solution containing 40% n-propanol by volume.

9. An active peptide fraction containing immunopotentiating thymic polypeptides including thymosin $\beta_4$, thymosin $\beta_9$ and prepared from freshly frozen thymus tissue by a process comprising:
   (1) homogenizing the tissue in the presence of an ice cold aqueous solution containing an effective amount of guanidinium salt,
   (2) suspending the resulting homogenate in a pyridine-formic acid solution at about pH 4.0,
   (3) centrifuging the resulting suspension and obtaining the resulting supernatant, (4) ultrafiltering the resulting supernatant through ultrafilters having a molecular weight cut-off of 10,000 daltons,
(5) submitting the resulting filtrate to a reverse phase hydrophobic resin,
(6) washing said resin with pyridine-formic acid buffer solution of about pH 4.0, and
(7) collecting the material eluting from said resin upon applying the same buffer solution containing 40% by volume n-propanol, to provide thereby the active peptide fraction.

10. A process for isolating selected polypeptides from a freshly frozen biological specimen, the process comprising in sequence treating the specimen with an effective amount of guanidinium salt and separating the selected polypeptides from said specimen.

11. A process according to claim 10 wherein the specimen is animal tissue.

12. A process according to claim 11 wherein the animal tissue is calf thymus or calf spleen.

13. A process according to claim 10 wherein the guanidinium salt is guanidine hydrochloride.

14. A process according to claim 10 wherein the selected polypeptides are separated from the specimen by ultrafiltration and chromatographic methods.

15. A process according to claim 14 wherein the chromatographic methods comprise high pressure liquid chromatography and a reverse phase hydrophobic resin thereto.

16. A method for preventing and treating opportunistic infections in immunosuppressed subjects, which method comprises administering to the subject in immunopotentiating effective amount of an active peptide fraction of any one of claims 1-8.

17. An active peptide fraction containing immunopentiating thymic polypeptides, prepared from freshly frozen thymic tissue by a process comprising:
(a) homogenizing the frozen tissue to provide a frozen powder and adding said powder to an aqueous cold solution containing an effective amount of a guanidinium salt, and
(b) isolating from the resulting homogenate the peptide material therein by an isolation method comprising ultrafiltration through ultrafilters having a molecular weight cut-off of 10,000 daltons and absorption on and elution from a reverse phase hydrophobic resin with a miscible solvent capable of eluting and providing thereby the active peptide fraction.

18. A fraction according to claim 17 wherein the polypeptides contained by said fraction comprise thymosin $\beta_4$ and thymosin $\beta_9$.

19. A fraction according to claim 17 wherein the thymic tissue is calf thymus or calf spleen.

20. A fraction according to claim 17 wherein the guanidinium salt is a guanidine hydrohalide.

21. A fraction according to claim 20 wherein the guanidine hydrohalide is guanidine hydrochloride.

22. A fraction according to claim 17 wherein said resin is a hydrocarbon of $C_8$ to $C_{18}$ on an inert matrix, said matrix being inert to said solvent.

23. A fraction according to claim 22 wherein the inert matrix is selected from the group consisting of silica gel, glass and polysaccharides.

24. A fraction according to claim 17 wherein said fraction is obtained from said resin by eluting said resin with a pyridine-formic acid buffer solution of about pH 4.0, said solution containing 40% n-propanol by volume.

* * * * *